US008367399B2

(12) United States Patent
Bellini et al.

(10) Patent No.: US 8,367,399 B2
(45) Date of Patent: Feb. 5, 2013

(54) METHOD FOR MEASURING MOLECULAR INTERACTIONS BY MEASUREMENT OF LIGHT REFLECTED BY PLANAR SURFACES

(75) Inventors: Tommaso Bellini, Milan (IT); Marco Buscaglia, Milan (IT); Stefano Pezzati, Milan (IT)

(73) Assignee: Universita' degli Studi di Milano, Milan (IT)

( * ) Notice: Subject to any disclaimer, the term of this patent is extended or adjusted under 35 U.S.C. 154(b) by 590 days.

(21) Appl. No.: 12/293,038

(22) PCT Filed: Mar. 14, 2007

(86) PCT No.: PCT/IB2007/000618
§ 371 (c)(1),
(2), (4) Date: Sep. 15, 2008

(87) PCT Pub. No.: WO2007/105081
PCT Pub. Date: Sep. 20, 2007

(65) Prior Publication Data
US 2010/0227336 A1 Sep. 9, 2010

(30) Foreign Application Priority Data

Mar. 16, 2006 (IT) .............................. MI2006A0477

(51) Int. Cl.
*C12M 1/34* (2006.01)
*C12M 3/00* (2006.01)
(52) U.S. Cl. ............... 435/288.7; 435/283.1; 435/287.1; 435/287.2; 436/518; 436/501

(58) Field of Classification Search ............... 435/283.1, 435/287.1, 287.2, 288.7; 436/518, 501
See application file for complete search history.

(56) References Cited

U.S. PATENT DOCUMENTS

| 5,324,633 | A | 6/1994 | Fodor et al. | |
| 5,482,830 | A * | 1/1996 | Bogart et al. | 435/5 |
| 7,396,676 | B2 * | 7/2008 | Robotti et al. | 435/287.2 |
| 2004/0096985 | A1 * | 5/2004 | Kenjyou et al. | 436/514 |
| 2004/0146715 | A1 * | 7/2004 | Guire et al. | 428/412 |
| 2007/0196819 | A1 * | 8/2007 | Asberg et al. | 435/5 |

OTHER PUBLICATIONS

Guenter Gauglitz, "Direct optical sensors: principles and selected applications", Analytical and Bioanalytical Chemistry, vol. 381, No. 1, Jan. 1, 2005, pp. 141-155, XP019327063.
Sadowski JW, "Review of optical methods in immunosensing", Proc. SPIE, vol. 954, 1988, pp. 413-419, XP009087958.
International search report in corresponding PCT/IB2007/000618, Aug. 2007.

* cited by examiner

*Primary Examiner* — Melanie J Yu
(74) *Attorney, Agent, or Firm* — Young & Thompson

(57) ABSTRACT

A procedure for the quantitative determination of interactions of ligands with receptors adsorbed or immobilized on the surface of a solid material which can be functionalized, transparent and with low refractive index, by direct measure of the reflection of light. The procedure includes utilizing a planar surface, flat or rough, of a transparent solid material formed from a hydrophobic amorphous polymer, having a refractive index between 1.3200 and 1.3500, which is brought into a solution of a mixture containing from 1 nanogram/ml to 10 milligrams/ml in concentration of molecules with a function of receptor or reagent.

14 Claims, 5 Drawing Sheets

METHOD FOR MEASURING MOLECULAR INTERACTIONS BY MEASUREMENT OF LIGHT REFLECTED BY PLANAR SURFACES

BACKGROUND OF THE INVENTION

1. Field of the Invention

The present invention relates to a simple and efficient method for the quantitative determination of ligand interactions with receptors adsorbed or immobilized on the surface of a solid material by direct measurement of the reflected light intensity.

More specifically, the present invention refers to a method for the quantitative determination of ligand interactions with receptors wherein planar surfaces of materials, having a refractive index between 1.32 and 1.35, are used.

2. Description of the Related Art

In the prior art, several methods to determine interactions between ligands and receptors, that is the binding affinities of ligand-receptor reversible systems, of chemical, biochemical or biological interest have been reported. A list is reported in Angew. Chem. Int. Ed. 1998, 37, page 2785. The known methods generally comprise the receptor immobilization on a suitable flat surface and the direct or indirect measurement of the variations of certain surface properties, for example the optical ones, after the ligands enter into contact with the surface. The variations are due to the formation of ligand/receptor couples.

One class of these methods requires the labeling of the ligand in solution, that is the covalent modification of the ligand with fluorescent, luminescent or radioactive species (see for example patent application US 2004/0014060 A1). However, it is to be noted that the modification of ligand is very complex and long and difficult to be used in screening tests where numerous different ligands are used. Furthermore, the methods require an additional operation for removing, by washing out, the free ligands, those which have not interacted with the receptors and which interfere with the measurement. A further drawback of said method is that the ligand-receptor interaction can be influenced by the chemical modification of the ligand due to labeling.

Another class of methods which simulated more effectively the ligand-receptor interactions (for example those occurring on a cell membrane surface), directly exploits the variations induced on a surface by the bond formation in the ligand-receptor couple, without modifying the ligand with labeling substances. An example of this method uses the biosensor BIAcore, marketed by GE Healthcare (Uppsala, Sweden). See for example U.S. Pat. No. 5,313,264 and U.S. Pat. No. 5,374,563. In this biosensor, wherein the principle of Surface Plasmon Resonance (SPR) is used (see the publication Jiri Homola, Sinclair S. Yee, Gunter Gauglitz, Surface plasmon resonance sensors: review, Sensors and Actuators B, vol. 54 (1999), pages 3-15), an evanescent optical wave couples with surface plasmons of thin layers (50 nm) of conducting materials such as silver or gold, and generates a resonance phenomenon at specific angles. This allows determining the variation of the refractive index of the layer of immobilized material on the metal, for example a ligand-receptor couple. The binding constants between ligand and receptor are obtained from this variation.

This method, even though it is very used in practice, is rather complicated and expensive and it is not always accurate in the determination of the binding constants. See for example the publication "Use of surface plasmon resonance to probe the equilibrium and dynamic aspects of interactions between biological macromolecules", by Peter Schuck, Annu. Rev. Biophys. Biomol. Struct., 1997, 26, pages 541-566. In fact, said method is based on an indirect detection of the adsorbed mass by the effect that it has on the propagation velocity of a plasmon, which in turn determines the coupling angle of a laser beam.

The problems connected to the use of the BIAcore method for the determination of the binding constants mostly depend on the complexity of the method:

- the measured signal depends on the physical properties of five different materials through a complex functional dependence including parameters not known a priori; the five mentioned materials are: the glass support or similar products, the thin layer of the conductor deposited on the support, the polymeric layer which allows to functionalize the metallic surface, the molecules adhering because of the interaction and the aqueous solution;
- the sensitivity and accuracy of the measurement strongly depend on the thickness and the surface quality of the conductor layer forming the sensor (see the publication "Optical properties and instrumental performances of thin gold films near the surface plasmon resonance" by H. Neff et al., Thin solid films, 2006, 496, pages 688-697);
- the measurements are based on the detection of the light intensity at various angles and this requires an equipment capable of high resolution angular scanning and thus it is composed by high precision moving parts or photodetector matrices of suitable space resolution (see the article "Quantitative interpretation of the response of surface plasmon resonance sensors to adsorbed films" by L. S. Jung et al, Langmuir, 1998, 14, pages 5636-5648).

Said problems produce:
- the non agreement between the affinity constant values determined through the binding kinetics and those obtained at the thermodynamic equilibrium;
- the impossibility to predict the intensity of the signal generated when ligand/receptor couples are formed on the surface, since the signal depends on not previously known parameters.

The need was therefore felt to have available a simple method for the determination of interactions between ligands and receptors directly exploiting the variations induced by the ligand-receptor interaction on a surface, avoiding the ligand labeling operations, allowing the determination of the affinity constant values under thermodynamic equilibrium conditions, thus avoiding the drawbacks of the indirect methods, such as, for example, BIAcore, and allowing the use of the method also in the study of multivalent ligands, since most of the ligands of biological and pharmacological interest have multiple binding sites. In particular, the need was felt for a high sensitivity method, whose signal was detectable by means of instrumentation simple to build, and was quantitatively interpretable through previously known parameters, overcoming, in this way, the prior art drawbacks.

SUMMARY OF THE INVENTION

It has been now unexpectedly and surprisingly found that it is possible to overcome the said drawbacks with a quantitative optical method which allows the determination of the binding affinity of interacting molecular species and of their concentration by means of the method described hereinafter.

It is object of the present invention a method for the determination of the binding constant of two interacting molecular species and/or of the concentration of a ligand in solution by using measurements of the intensity of reflected light, comprising the following steps:

a) a planar surface, flat or rough, of a transparent solid material constituted by a hydrophobic amorphous polymer, having a refractive index between 1.3200 and 1.3500, preferably between 1.3300 and 1.3350, is brought into contact with an aqueous or non-aqueous solution of a mixture containing from 1 nanogram/ml to 10 milligrams/ml in concentration of molecules with a function of receptor or reagent, such as antibodies or other proteic or peptidic complexes, or nucleic acids, or lipids, or amphiphilic surfactants or block polymers ended with a receptor or reagent, optionally mixed to other molecules (spacers) having no receptor function, optionally measuring at each addition the light intensity reflected from the interface between the aqueous solution and the said solid material and reporting the measured value on a diagram as a function of time or as a function of the receptor concentration progressively added, optionally repeating this procedure by bringing the surface into contact with other aqueous or non-aqueous solutions of the said molecules;

b) addition to the solution obtained in step (a) of a sequence of known volumes of an aqueous solution of a ligand, measuring at each addition the light intensity reflected from the interface between the aqueous solution and the polymeric material and reporting the measured value on a diagram in connection as a function of the time or as a function of the ligand concentration [$T_0$] progressively added, and fitting the reflected light intensity data I as a function of the ligand additions with the formula:

$$I = cI_0(R^\perp \sin^2\phi + R^\| \cos^2\phi) + I_N \qquad (1)$$

wherein
$I_0$ represents the intensity of light incident on the surface,
c is a factor taking into account the surface roughness and has a value equal to
1 only in the case of a surface without roughness,
$I_N$ is the light intensity measured by the detector in the absence of the interface,
$\phi$ is the angle formed by the direction of the light polarization with the incidence plane,
$R^\perp$ and $R^\|$ are the reflection coefficients drawn from the Fresnel formulas for a thin layer in the case of polarization perpendicular and parallel to the incidence plane, respectively, and they depend on the amount of ligand in contact in every instant with the receptors adsorbed on the interface. From said fitting, the concentration of ligand [$T_L$] interacting with the receptors on the surface, and optionally, by means of the Langmuir absorption formula, the K constant of receptor-ligand binding are obtained.

BRIEF DESCRIPTION OF THE DRAWING FIGURES

FIG. 1. is a diagram representing the intensity of the reflected light measured in equilibrium conditions as a function of the concentration in the cell of Avidine (squares) and Bovine Serum Albumin conjugated with biotin (circles).

Figure 4:
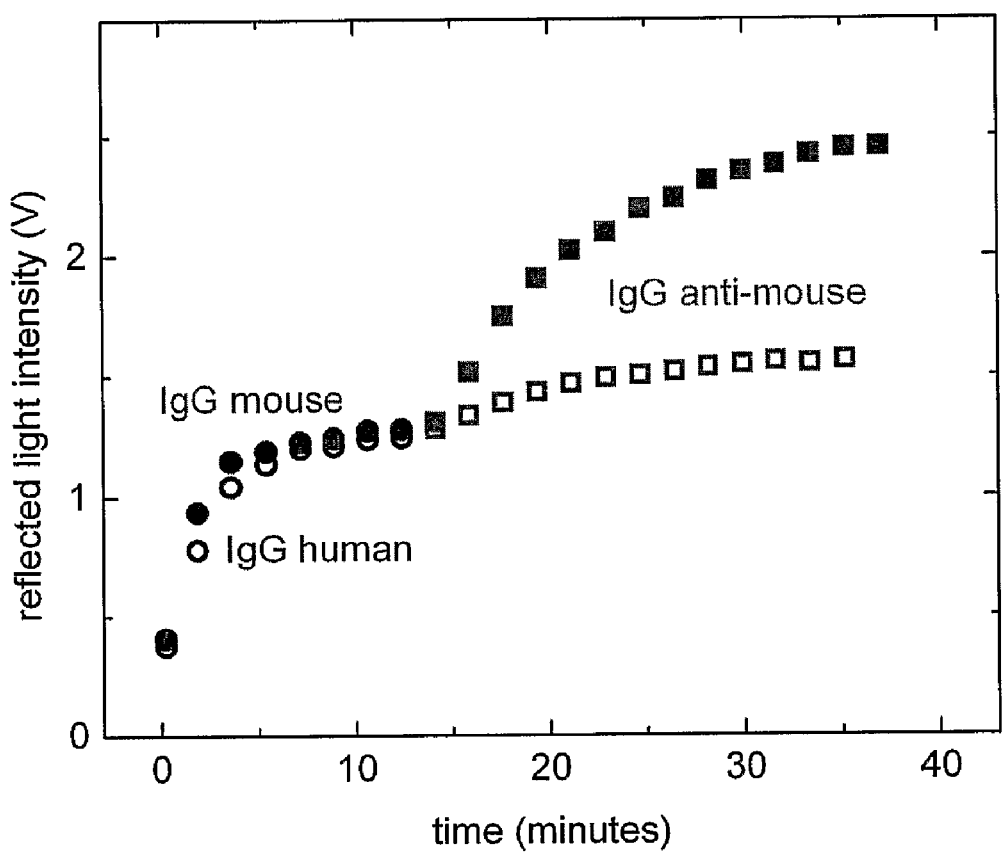

FIG. 4 is a diagram representing the intensity of the reflected light measured as a function of time in two experiments. In the first experiment (full symbols), at time=0 minutes a solution containing mouse IgG antibodies is flowed in the flow cell (full circles) followed, at time=15 minutes, by a solution containing anti-mouse IgG antibodies (full squares). In the second experiment (hollow symbols), at time=0 minutes a solution containing human IgG antibodies is flowed in the flow cell (hollow circles) followed, at time=15 minutes, by a solution containing anti-mouse IgG antibodies is flowed in the flow cell (hollow squares).

Figure 5:
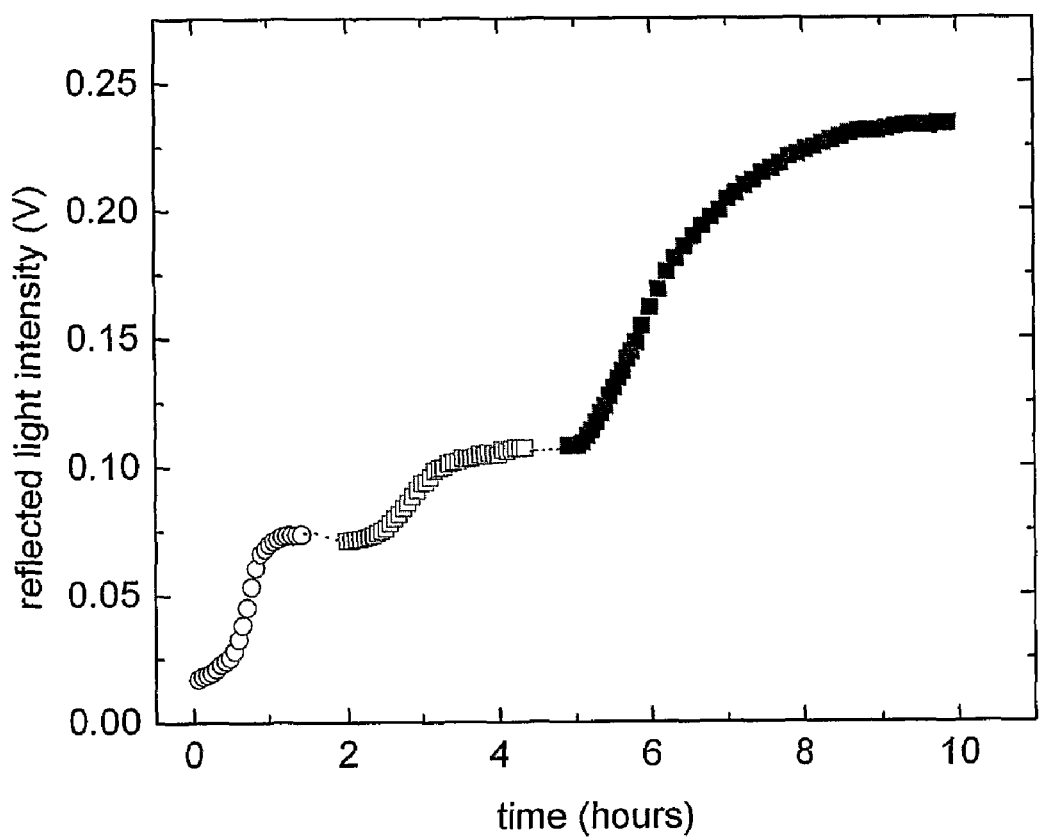

FIG. 5 is a diagram representing the intensity of the reflected light measured as a function of time. At time=0 hours a solution containing Avidine (hollow circles) is flowed in the flow cell (hollow circles) followed, at time=2 hours, by a solution containing anti-human IgG antibodies conjugated with biotine (hollow squares) and, at time=4.5 hours, by a solution containing human IgG antibodies (full squares).

DETAILED DESCRIPTION OF THE INVENTION

The Fresnel formulae for the thin layer are those, for example, described in Frank L. Pedrotti e Leno S. Pedrotti, "Introduction to Optics—Second Edition", Prentice Hall, Upper Saddle River, N.J., 1993, pages 392-396.

The amount of ligand bound to the receptor in equilibrium conditions as a function of the ligand additions can be expressed by a function known as "Langmuir isotherm", which depends on the receptor concentration and on the affinity constant, also said binding constant. For the Langmuir isotherm see, for example, Paul C. Hiemenez, "Principles of Colloid and Surface Chemistry", Marcel Dekker, New York, 1997, pages 287-298.

The fitting of the reflected intensity data is performed inserting the volume of receptors and ligands adsorbed or immobilized on the surface in the Fresnel formulas for the thin layer reflection. This produces a function depending on the refractive indexes of water, polymeric material and material on the surface, as well as on the receptor and ligand surface concentration and on the affinity constant. Since the other parameters are generally known or measurable, from the fitting it is possible to obtain the concentration of ligands interacting with the receptors and the affinity constant.

The method of the present invention is applicable for transparent or turbid and/or absorbing solutions, according to the relation shown in formula (1). Moreover, the method of the present invention is applicable for any incidence angle and any light polarization.

The ratio between the variation of the light intensity due to the formation of successive molecular layers on the surface and the background light intensity measured before step (a) or step (b) can be varied to improve the sensitivity of the method, either modifying the incidence angle and/or the light collection angle, or by changing the polarization of the incident light and/or measuring the polarization variations of the detected light.

For example, in the case of light incidence angle of 45°, of polarization perpendicular to the incidence plane ($\phi$=90°), of difference $\Delta n$ between the refractive indexes of the aqueous solution and of the polymeric substratum lower than or equal to 0.012, and of thickness of the molecular layer of adsorbed or immobilized receptors and interacting ligands lower than 15 nanometers, assuming the refractive indexes of receptor and ligand molecules to be equal and having value $n_a$, the intensity I reflected from the flat smooth surface can be expressed according to the following formula (2) approximated with an error lower than 1% with respect to the complete equation (1):

$$I = 2I_0 \left(\frac{\pi V N_a}{\lambda A}\right)^2 \frac{(n_a^2 - n_0^2)(n_a^2 n_0 - n_0^3 + 2n_a^2 \Delta n)}{n_0^3} \left(\frac{m_R [T_R]}{\rho_R} + \frac{m_L [T_L]}{\rho_L}\right)^2 + I_b \quad (2)$$

wherein
$I_o$, $[T_L]$, $\Delta n$ are as above defined,
$[T_R]$ is the concentration of receptors adhered to the surface,
$m_R$ e $m_L$ are the molecular weight of the receptor and the ligand, respectively,
$\rho_R$ e $\rho_L$ represent the density of the receptor and the ligand, respectively,
V is the volume of the aqueous solution,
A is the area of the solid material surface on which the receptor and ligand interaction takes place,
$\lambda$ the wavelength of the incident light,
$N_a$ is the Avogadro number,
$n_0$ is the refractive index of the aqueous solution, and
$I_b$, the intensity measured before the addition of receptors (before step (a)).

The concentration $[T_L]$ of ligand adhering to the surface in a state of thermodynamic equilibrium can be expressed by the Langmuir adsorption formula (3):

$$[T_L] = [T_0] + K^{-1} + [S_0] - \sqrt{([T_0] + K^{-1} + [S_0])^2 - 4[T_0][S_0]} \quad (3)$$

wherein
$[T_0]$ is as above defined,
$[S_0]$ is the molar concentration of ligand-receptor binding sites, and
K is the affinity constant (also said binding constant).

The other parameters being know, meaning that they are measurable or already known, by fitting the equation (2) to the measured values of reflected intensity, the concentration $[S_0]$ of receptors adsorbed or immobilized on the surface and the affinity constant K for the ligand-receptor interaction are obtained.

The hydrophobic amorphous polymer can be, for example, a perfluoropolymer. The surface of amorphous polymeric material can be included in a cell for measures in the absence of flow, or it can be included in a measuring cell having the possibility of flowing the solution, or it can be included in an immersion probe. The surface of polymeric material can be part of a polymeric manufactured article which can have different shapes, such as, for example, the shape of prism or frustum of prism, of plaque with parallel or non parallel faces, of thin film with thickness preferably higher than 1 micron. The polymeric manufactured article can be obtained by known techniques such as: molding, extrusion, film formation through casting, spin-coating. The surface roughness of the films can be controlled during the film formation, for example by selecting solvents and evaporation temperatures and annealing. Other methods for controlling the surface roughness on an already formed surface consist in the use of solvents, lapping and imprinting operations.

The polymeric surface can be smooth or can present a regular or irregular roughness, having characteristic size of the depth and of the width of the surface roughness between 10 nanometers and 3 millimeters. The polymer surface roughness can produce a component of diffused light which however is not a disadvantage of the present method, as it is proportional to the molecular layers covering the surface, analogously to the reflected light. In this case it is possible to measure the light intensity also in a different direction from that of the geometrical reflection.

As molecules or molecular complexes with the function of receptor, those generating a monolayer adsorbed or immobilized on the solid surface are used. The adsorption can be due to hydrophobic or electrostatic interactions between the receptor molecules and the solid surface. The immobilization can be due to, in addition to direct adsorption of the receptor molecules, to the formation of chemical bonds between the receptor molecules and the amorphous polymer constituting the solid surface, or with a different compound adsorbed or immobilized to the solid surface, for example through coating or deposition techniques. The molecules or the molecular complexes with the function of receptors can be immobilized and/or chemically modified through methods of the known art, such as chemical methods or electromagnetic irradiation or plasma treatment methods.

The molecules or the molecular complexes with the function of ligand, after their immobilization on the surface through the interaction with the receptors, can, in turn, play the function of receptor for other molecules or molecular complexes interacting with them.

As said, surfactants can be used as receptors, for example those non ionic amphiphilic generating a self assembled monolayer on the solid surface. The formation of said monolayer can be verified by carrying out step (a) of the present method and observing the achievement of an asymptotic value of the light intensity measured at equilibrium as a function of the receptor concentration progressively added.

The receptor molecules, as said, can be used in admixture with spacer molecules which don't have receptor function. Generally, the latter can be selected between surfactants and proteins. Moreover, the molecules used as spacers must not have specific interactions. The absence of said interaction can be determined by carrying out step (a) of the method according to the invention using only spacer molecules, and then carrying out step (b) verifying the absence of variations of the reflected light intensity.

The surfactants, either bringing a receptor function or used as spacer molecules, can be selected among non-ionic surfactants, for example glycolipids, oligo-oxyethilenes, oligo-oxypropylenes or alkyl-glycoxides; or among ionic surfactants: for example anionic such as sodium bis(2-ethylhexyl)sulphosuccinate (AOT), or cationic such as didodecyl-dimethylammonium bromide (DDAB).

The surfactants ending with a receptor are prepared by reacting the above described surfactants with receptors according to known processes of the prior art.

The ligand-receptor couple is defined as a couple of molecules, for example proteins, nucleic acids, glycoproteins, carbohydrates, hormones having an affinity capable of forming a more or less stable bond. In particular antibody/antigen, enzyme/inhibitor, carbohydrate/carbohydrate, protein/DNA, DNA/DNA, peptide/peptide can be mentioned.

In steps (a) and (b) of the method according to the invention, the measurements of the reflected light intensities are carried out by detecting the intensity of the reflected light, at more or less regular intervals of time, for example of 1 second or longer, until reaching a constant value. It has been found that the time necessary for reaching the thermodynamic equilibrium depends on the specific type of receptor-ligand couple. Therefore the performed measurements can allow the evaluation of the adsorption-desorption kinetics.

The method of the present invention allows to detect 100 picograms of ligand on a surface of 1 mm² without intrinsic limits on the minimum concentration in solution, corresponding to a sensitivity limit of the order of the most sensitive techniques of the prior art. The measurement surface area is defined as the surface on which the receptor is adsorbed or immobilized. Such area can be reduced to have a characteristic diameter of few tens of microns, thus allowing the detection of few picograms of ligand. The whole measurement surface can be composed of different smaller surfaces, on which are adsorbed or immobilized different receptors.

It is surprising and unexpected that the reflection of the light turned out to be effective in identifying and measuring directly, through measurement of reflected light intensity, the interactions between receptors and ligands according to the method of the present invention.

Some examples follow with illustrative but not limitative purposes of the present invention.

EXAMPLES

Example 1

Measure of the Binding Constant Between the Protein Bovine Serum Albumin Conjugated with Biotin (Biotinated BSA, Ligand) and Avidin (Receptor)

Step (a)

A right angle prism of a copolymer of TFE containing 60% by moles of perfluorodioxole TTD, having a 1 cm side and smooth surface mechanically worked by lapping, is immersed in 1.5 milliliters of water.

A light beam coming from a 5 milliWatt He—Ne laser impinges perpendicularly on the right angle prism face not in contact with the aqueous solution. The reflection takes place at the interface between the longer side of the prism and the aqueous solution put into contact with it. The reflected beam comes out from the second smaller side of the prism and is detected by an amplified photodiode which converts the reflected light intensity into an electric signal.

A 5 micromolar aqueous solution of protein Avidin (commercialized by Aldrich, cas. No. 1405-69-2) is added to the water, in 10 microliters portions, for a total of 80 microliters. The solution is constantly kept under stirring.

Figure 1:
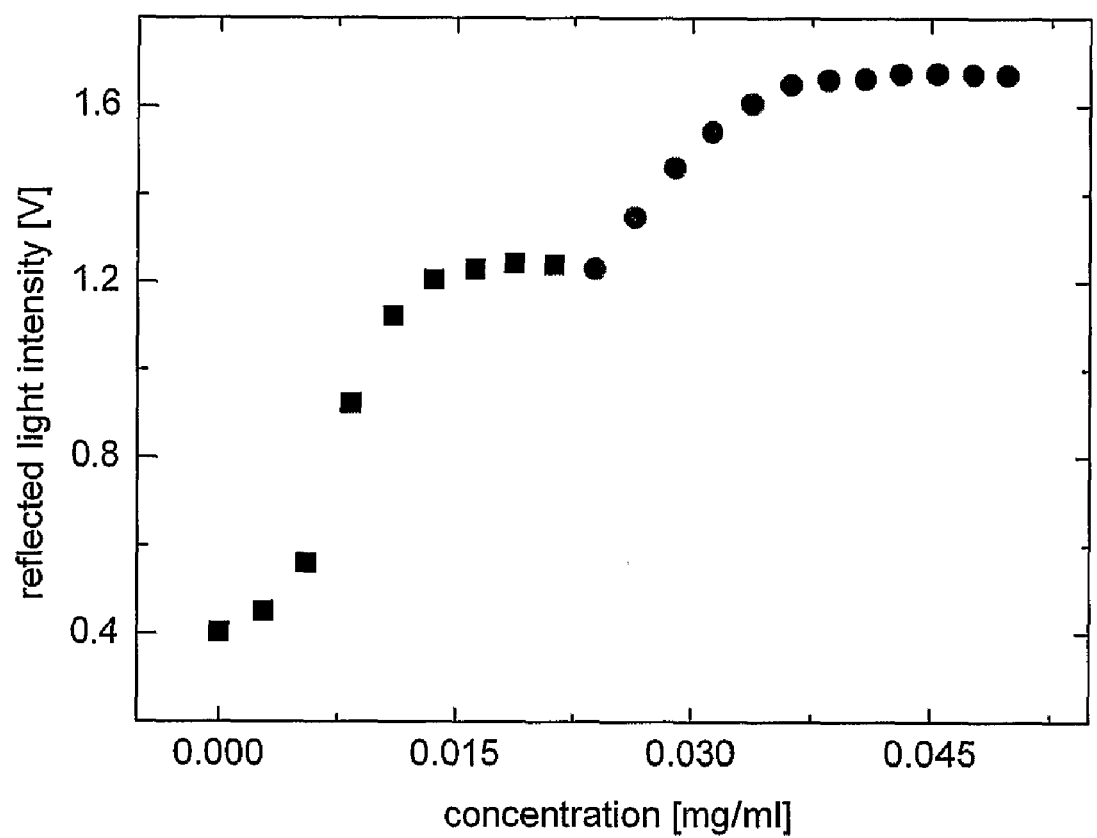

After each addition the intensity of the light reflected from the prism face is measured until a stable value is reached. The intensity values measured at equilibrium (squares in FIG. 1) are reported in a diagram as a function of the concentration of Avidin in the cell, expressed in mg/ml, obtaining the curve reported in FIG. 1 hereinafter.

The progressive covering of the face immersed into the solution by the added protein is observable from the variation of the light intensity measured by the photodiode.

The complete covering is clearly shown by the achievement of an asymptotic value of the measured light intensity.

Step (b)

To the solution obtained in step (a), in which the prism is immersed, when the asymptotic value is reached, a 5 micromolar aqueous solution of Bovine Serum Albumin conjugated with biotin (marketed by Pierce, prod. No. 29130), is added at 10 microliters portions. The solution is constantly kept under stirring. After each addition the reflected light intensity is measured as in step (a).

The values of measured intensity (dots in FIG. 1) are reported in a diagram as a function of the obtained concentration of proteins and added to the curve diagrammed in step (a).

The formation of the BSA-biotin-Avidin bonds is detected from the increase of the measured light intensity until an asymptotic value is reached, indicating saturation of the Avidin binding sites with biotin.

By fitting the Langmuir adsorption formula to the reflected light intensity data as a function of the additions of BSA-biotin, the receptor-ligand binding constant is obtained. The binding constant obtained is $2.6 \times 10^9$ liters×moles$^{-1}$.

Example 2

Measure of the Binding Constant Between Avidin (Receptor) and Bovine Serum Albumin Conjugated with Biotin (Biotinated BSA, Ligand) by Means of a Thin Film The Example 1 is repeated replacing the prism with a thin film of the same copolymer used in Example 1, having a thickness of 17 micrometers. Said film is mounted into a Plexiglas frame of square shape having a sustaining function with an external side of 1.4 cm and internal side of 0.4 cm.

A laser light beam impinges on said film as in the Example 1, with an angle of 45° respect to the film surface. An amplified photodiode, placed at 90° respect to the direction of the beam coming out from the laser, converts the light intensity into an electric signal.

All the operations described in the Example 1 are then repeated obtaining a binding constant of $3.7 \times 10^9$ liters×moles$^{-1}$.

Example 3

Detection of the Interaction Between Avidin (Receptor) and Bovine Serum Abumin Conjugated with Biotin (Biotinated BSA, Ligand) in a Solution with High Extinction Coefficient It has been used the measurement system described Example 1 constituted by a right angle prism made of a copolymer of TFE immersed in water, a He—Ne laser and a photodiode placed as in Example 1.

The prism is immersed in 1.5 milliliters of water to which it is added a volume of 10 microliters of aqueous solution containing 10 micrograms of protein Avidin. The solution is constantly kept under stirring.

Figure 2:
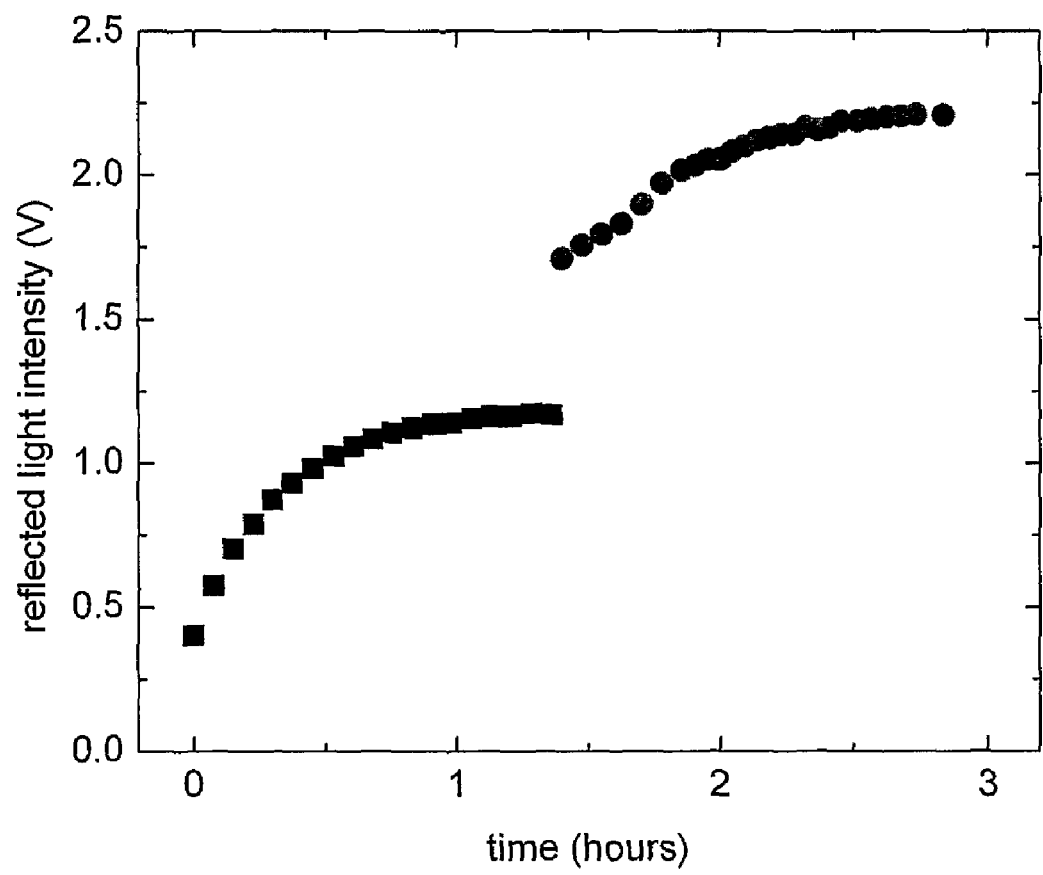
FIG. 2 is a diagram representing the intensity of the reflected light measured as a function of time. At time=0 hours a solution containing Avidine is added in the cell (squares), at time=1.5 hours, immediately after the addition of a solution of iron oxide sub-micron sized particles, a solution containing Bovine Serum Albumin conjugated with biotin is added in the cell (circles).

The intensity of the light reflected by the prism face is measured at regular intervals of 2 minutes and the measured intensity values (squares in FIG. 2) are reported in a diagram as a function of time until reaching a stable value.

To the solution, constantly kept under stirring, it is added a volume of 100 microliters of a colloidal suspension containing 0.1% (vol/vol) of sub-micron sized iron oxide particles, conferring an extinction coefficient of 5 cm$^{-1}$, that is a value higher than the one reported in the literature for whole blood at a wavelength of 633 nm.

The intensity of the reflected light measured by the photodiode rapidly increases by nearly 50% because of the increase of the refractive index of the aqueous solution after the addition of the particulate.

After 2 minutes, it is added a volume of 10 microliters of an aqueous solution containing 10 micrograms of protein Bovine Serum Albumin conjugated with biotin (marketed by Pierce, prod. No. 29130).

The intensity of the light reflected by the prism face is measured at regular intervals of 2 minutes, and the measured intensity values (dots in FIG. 2) are reported in a diagram as a function of time, until reaching a stable value.

It is obtained an increment of the output voltage of the photodiode due to the addition of BSA-biotin of about 0.5 volt, comparable to what has been measured in Example 1 in a transparent aqueous solution, without particulate. This shows that the presence of an absorbing and scattering medium does not limit significantly the detection of the interaction between adsorbed Avidin and BSA-biotin in solution.

Example 4

Figure 3:
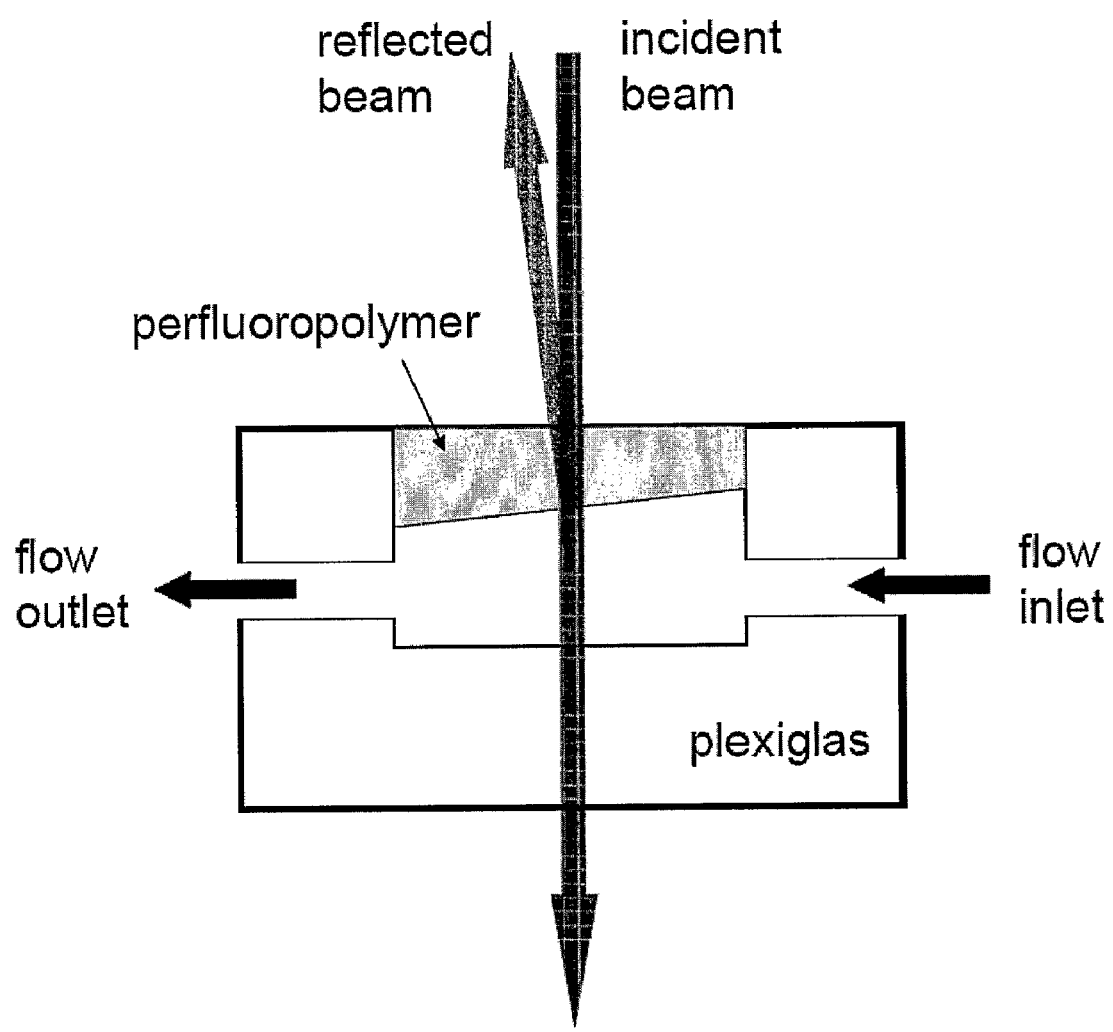
FIG. 3 is a diagrammatic representation of a flow cell.

Detection in a Flow Cell of Mouse IgG Antibodies by the Interaction with Anti-Mouse IgG Antibodies A flow cell with internal volume of about 100 microliters has been obtained from a Plexiglas parallelepiped with size 2 cm×2 cm×3 cm as reported in FIG. 3. A cell side has a window made of a copolymer of TFE containing 60% by moles of perfluorodioxole TTD (dark element in FIG. 3). The window surface facing the intern of the cell forms an angle of 5° with the external surface. The cell is connected with extern by means of two tubes with diameter of 1 mm.

A light beam from a 5 milliWatt He—Ne laser impinges perpendicularly on the external face of the window of perfluorinated material. The reflected light coming from the interface between aqueous solution and perfluoropolymer, having a direction forming an angle of about 5° respect to the normal of the external surface, is detected by an amplified photodiode converting the reflected light intensity into an electrical signal.

Step (a)

Into the cell it is flowed at 20 microliters/minute an aqueous solution containing mouse IgG antibody at a concentration of 5 micromolar. During the flow, the intensity of the light reflected from the interface between aqueous solution and perfluoropolymer is measured at intervals of 2 minutes. The measured intensity values (full dots in FIG. 4) are reported in a diagram as a function of time, until reaching an asymptotic value.

Step (b)

In the cell it is flowed at 20 microliters/minute an aqueous solution containing anti-mouse IgG antibody made in goat at a concentration of 5 micromolar. The intensity of the reflected light is detected as in step (a) and the values are reported in a diagram as a function of time (full squares in FIG. 4). After 20 minutes it is obtained an increment of the intensity of the reflected light of nearly 100% respect to the value measure at the end of step (a).

Example 5

Control Experiment for the Detection of the Absence of Specific Interactions Between Human IgG Antibodies and Anti-Mouse IgG Antibodies The flow cell described in Example 4 is cleaned by means of a continuous flow for 3 hours of an aqueous solution containing 1 molar sodium hydroxide. After this operation, the measured value of the intensity of reflected light is found to be equal to the one measured before step (a) of Example 4.

Step (a)

The procedure described in step (a) of Example 4 is repeated using human IgG antibody instead of mouse IgG antibody. The reflected light intensity is detected as in step (a) of Example 4 and the values are reported in a diagram as a function of time (open dots in FIG. 4).

Step (b)

Then, the procedure described in step (b) of Example 4 is repeated identically using anti-mouse IgG antibody made in goat. The intensity of the reflected light is measured as in step (b) of Example 4 and the values are reported in a diagram as a function of time (open squares in FIG. 4). After 20 minutes the intensity of the reflected light increases by about 20% compared to the value measured at the end of step (a). The obtained increment is much lower than the one obtained at the end of the step (b) of Example 4 and it is attributed to the a specific interaction between anti-mouse IgG antibodies and the human IgG antibodies adsorbed on the surface during step (a).

Example 6

Detection of Human IgG Antibodies by Means of the Interaction with Anti-Human IgG Antibodies Conjugated with Biotin and Immobilized by Avidin A flow cell identical to the one described in Example 4, is filled with 100 microliters of water. The cell is flowed with an aqueous solution containing protein Avidin at the concentration of 1.5 micromolar for a total volume of 20 microliters. At the end of the flowing, the intensity of the reflected light detected by the photodiode is measured and diagrammed as a function of time (open dots of FIG. 5).

When a stable value of the reflected intensity is reached, any possible residual content of protein is eliminated with a washing-out procedure, consisting in applying a 20 microliters/minute flow of water for 50 minutes and, during flow, the reflected light intensity detected by the photodiode is measured and diagrammed as a function of time (dotted line in FIG. 5).

After the washing-out procedure, the cell is flowed with an aqueous solution containing anti-human IgG antibodies made in mouse conjugated with biotin at a concentration of 3 micromolar for a total volume of 20 microliters. At the end of the flowing, the reflected light intensity detected by the photodiode is measured and diagrammed as a function of time (open squares of FIG. 5) until a stable value is reached. The increase of the reflected light intensity detected by the photodiode is attributed to the adhesion of the antibody conjugated with biotin to the surface covered with Avidin.

When a stable value of the reflected intensity is reached, any possible residual content of antibody is eliminated by a washing-out procedure as above described and the value of reflected light intensity detected by the photodiode is measured and diagrammed as a function of time (dotted line in FIG. 5).

After the washing-out procedure, the cell is flowed with an aqueous solution of human IgG antibodies at the concentration of 2 micromolars for a total volume of 10 microliters. At the end of the flowing, the value of the reflected light intensity detected by the photodiode is measured and diagrammed as a function of time (filled squares of FIG. 5) until a stable value is reached. The increase of the reflected light intensity detected by the photodiode is attributed to the adhesion of the human IgG antibodies to the surface covered with anti-human IgG antibody.

The invention claimed is:

1. An optical method for determining a presence and strength of binding affinity of interacting molecular species, without requiring their labeling with fluorescent substances or with other kinds of luminescent or light absorbing probes, hereafter named receptor, being immobilized on a surface and the others, hereafter named ligands, being in a solution, or for determining a concentration of the ligands in the solution by using a measure of an intensity of a light reflected by a transparent assembly forming an interface between the solution and a solid material having a refractive index differing by no more than 0.1 from that of the solution, comprising the following steps:

a) a bare surface, flat or rough, of a transparent solid material constituted by a hydrophobic amorphous polymer, having a refractive index between 1.3200 and 1.3500, is brought into contact with an aqueous or non-aqueous solution of a mixture containing from 1 nanogram/ml to 10 milligrams/ml in concentration of molecules with a function of receptor or reagent, or antibodies or other proteic or peptidic complexes, or nucleic acids, or lipids, or amphiphilic surfactants or block polymers ended with a receptor or reagent, optionally mixed to other molecules having no receptor function, optionally measuring at each addition the light intensity reflected from the interface between the aqueous solution and said solid material and reporting the measured value on a diagram as a function of time or as a function of the receptor concentration progressively added, optionally repeating this procedure by bringing the surface into contact with other aqueous or non-aqueous solutions of said molecules;

b) addition to the solution obtained in step (a) of a sequence of known volumes of an aqueous solution of a ligand, measuring at each addition the light intensity reflected from the interface between the aqueous solution and the polymeric material and reporting the measured value on a diagram as a function of the time or as a function of the ligand concentration $[T_0]$ progressively added, and fitting the reflected light intensity data I as a function of the ligand additions with Fresnel formulas for thin layer reflection to obtain the adhered mass, and with a Langmuir formula for adsorption to obtain the strength of binding affinity of the ligand and the receptor at equilibrium or, if the strength of the binding affinity is known, to obtain the ligand concentration $[T_0]$.

2. The method according to claim 1, wherein the amphiphilic non ionic, or ionic, surfactants are surfactants which produce a monolayer on the polymeric surface.

3. The method according to claim 1, wherein the ligand-receptor couple is chosen among proteins, nucleic acids, glycoproteins, carbohydrates, or hormones.

4. The method according to claim 3, wherein the ligand-receptor couple of molecules is chosen among antibody/antigen, enzyme/inhibitor, carbohydrate/carbohydrate, protein/DNA, DNA/DNA, or peptide/peptide.

5. The method according to claim 1 wherein the receptors are at least one of immobilized or chemically modified via chemical methods, electromagnetic irradiation or plasma treatment methods.

6. The method according to claim 1, wherein the solution in contact with the surface of the solid material and containing the molecules or the molecular complexes having the function of at least one of receptors or ligands, is at least one of optically transparent, turbid or absorbing.

7. The method according to claim 1, wherein the surface of the solid material presents a regular or irregular roughness, having a surface roughness between 10 nanometers and 3 millimeters, and the intensity of the light emitted from the surface in presence of the ligand-receptor interaction is measured not only in a direction of a geometrical reflection but also in a direction different from that of the geometrical reflection.

8. The method according to claim 1, further comprising applying incident light having an incidence angle and a polarization of the incident light which optimize a ratio between the signal of reflected light in presence of the ligand-receptor interaction and the background noise due to reflection and scattering of light.

9. The method according to claim 8, wherein the reflected light is filtered by a polarizer whose orientation is chosen in order to optimize the ratio between the signal of reflected light in presence of the ligand-receptor interaction and the background noise due to reflection and scattering of light.

10. The method according to claim 1, wherein the surface of the polymeric amorphous material is embodied in a cell for measurements in the absence of flow, or is embodied in a flow cell, or is embodied in an immersion probe.

11. The method according to claim 1, wherein the surface of the polymeric material is divided in smaller areas, on which are adsorbed or immobilized different receptors.

12. The method according to claim 2, wherein the surface of the polymeric amorphous material is embodied in a cell for measurements in the absence of flow, or is embodied in a flow cell, or is embodied in an immersion probe.

13. The method according to claim 2, wherein the surface of the polymeric material is divided in smaller areas, on which are adsorbed or immobilized different receptors.

14. The method according to claim 1, wherein the refractive index is between 1.3300 and 1.3350.

* * * * *

UNITED STATES PATENT AND TRADEMARK OFFICE
CERTIFICATE OF CORRECTION

PATENT NO. : 8,367,399 B2  Page 1 of 1
APPLICATION NO. : 12/293038
DATED : February 5, 2013
INVENTOR(S) : Bellini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 695 days.

Signed and Sealed this

First Day of September, 2015

Michelle K. Lee
*Director of the United States Patent and Trademark Office*